United States Patent
Underwood (10) Patent No.: US 7,904,311 B2
(45) Date of Patent: Mar. 8, 2011

(54) MEDICAL MANAGEMENT MODELER AND ASSOCIATED METHODS

(75) Inventor: Howard R. Underwood, Bethesda, MD (US)

(73) Assignee: Aetna Inc., Hartford, CT (US)

( * ) Notice: Subject to any disclaimer, the term of this patent is extended or adjusted under 35 U.S.C. 154(b) by 405 days.

(21) Appl. No.: 12/033,694

(22) Filed: Feb. 19, 2008

(65) Prior Publication Data

US 2009/0043606 A1 Feb. 12, 2009

Related U.S. Application Data

(60) Provisional application No. 60/890,369, filed on Feb. 16, 2007.

(51) Int. Cl.
*G06Q 10/00* (2006.01)
*G06Q 50/00* (2006.01)

(52) U.S. Cl. .............. 705/2; 705/3; 705/4; 704/275
(58) Field of Classification Search .......... 705/2–4; 600/300; 704/275
See application file for complete search history.

(56) References Cited

U.S. PATENT DOCUMENTS

| | | | |
|---|---|---|---|
| 2005/0033607 A1* | 2/2005 | Georgiou et al. | 705/2 |
| 2007/0038516 A1* | 2/2007 | Apple et al. | 705/14 |
| 2008/0147411 A1* | 6/2008 | Dames et al. | 704/275 |

* cited by examiner

*Primary Examiner* — Luke Gilligan
(74) *Attorney, Agent, or Firm* — Leydig, Voit & Mayer, Ltd.

(57) ABSTRACT

A method and system for determining custom population Return on Investment (ROI) forecasted savings estimates for use in evaluating the desirability of active health care management programs and the depth of penetration of such programs. The method and system further include a graphical user interface and returns a statistical confidence of the predicted savings or loss.

15 Claims, 10 Drawing Sheets

Medical Management Modeler (MMM) - Phase I
Disease Management Program Impact Simulator To begin a model-driven Return on Investment (ROI) simulation, please complete the simulation-driver parameters referenced below then click "Continue". *Please note that simulation-driver values directly influence model simulation results.*

Please Select a Simulation Basis
- ◉ Book of Business Defaults with  ○ All members   ○ Exclude 65+ members
- ○ Client Specific Input

Please Select a Basis for Categorical Lives Input (if Client Specific Input selected above)
- ○ Members
- ○ Employees

Please Select a Pharmacy Rider Option
- ◉ Client Offering Aetna Pharmacy Coverage
- ○ Client Not Offering Aetna Pharmacy Coverage

Please Select One or More Disease Management Program(s) for Simulation
- ☑ Asthma
- ☐ Diabetes
- ☐ Congestive Heart Failure
- ☐ Coronary Artery Disease / Ischemic Heart Disease

MEDICAL MANAGEMENT MODELER AND ASSOCIATED METHODS

CROSS REFERENCE TO RELATED APPLICATION

This patent application claims the benefit of U.S. Provisional Patent Application No. 60/890,369, filed Feb. 16, 2007, which is incorporated by reference.

FIELD OF THE INVENTION

The invention generally relates to a statistical model-driven disease management program impact simulation tool that produces custom population Return on Investment (ROI) forecasted savings estimates. The simulation tool and associated methods are built on the underlying principles of demographic, geographic, health status and illness burden (i.e. risk) adjustment methodologies in order to simulate or predict estimated disease management program savings.

BACKGROUND OF THE INVENTION

Prior art approaches for determining an actionable metric, such as ROI, for evaluating the desirability of active health care management programs, and the depth of penetration of such programs, have proven inadequate. The results of such prior art calculations were not particularly accurate, often overstating or understating the actual outcomes, and such calculations further involved inefficient, cumbersome and time consuming processes. Consequently, there exists a need for a new and improved metric, and simplified systems and methods for generating such a metric, that more accurately simulates and/or forecasts expected program outcomes for a custom population.

SUMMARY OF THE INVENTION

In one aspect, the invention provides a method and system that uses robust statistical modeling techniques for determining a custom population ROI. According to the invention, a derived and controlled cohort is developed, which is then applied, via a control equation, to a validated set of inputs to obtain a monetary value or predicted utilization quantum. In addition, the methods and systems of the invention provide a statistical confidence level as to the savings or loss for a particular cohort. The invention helps reduce or eliminate bias, regression and trends analysis. In addition, the invention provides a simple and easy-to-use graphical user interface for inputting, validating and obtaining estimated disease management program savings.

The statistical model-driven disease management program impact simulation tools of the invention produce custom population Return on Investment (ROI) forecasted savings estimates for both direct costs, e.g., medical and pharmacy (when applicable), and indirect costs, e.g., productivity. The tools are built on the underlying principals of demographic, geographic, health status and illness burden (i.e. risk) adjustment methodologies, and scientific rigor is brought to bear on the simulation of, or, prediction for, estimated disease management program savings. These calculated savings are predicated on: (a) default, empirically-derived, chronically ill, Book of Business ("BOB") population characteristics, or, (b) dynamic user-input Request for Proposal ("RFP") population characteristics.

DETAILED DESCRIPTION OF THE INVENTION

Figure 1:
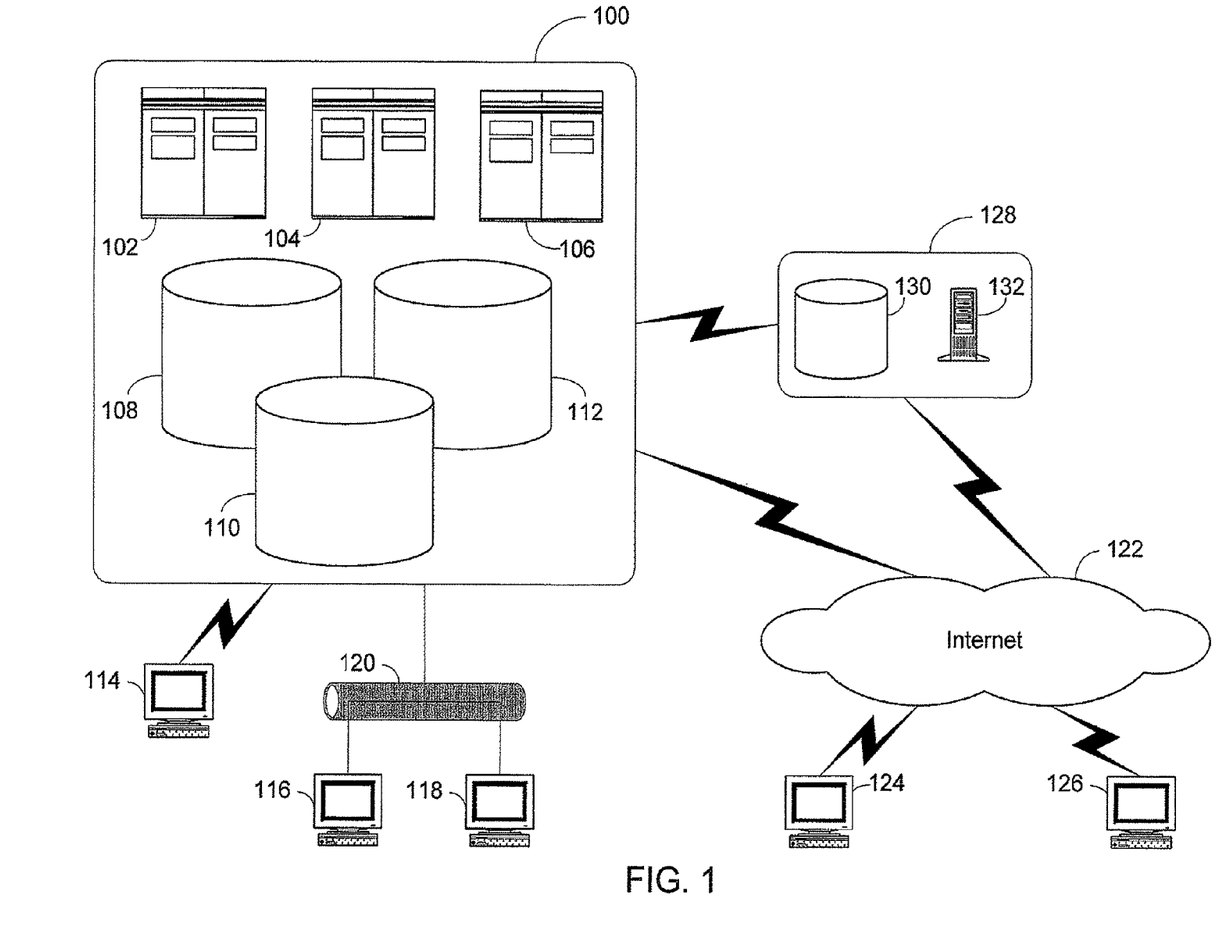
FIG. 1 schematically illustrates an exemplary environment in which the invention may be used.

FIG. 1 illustrates a logical arrangement of the environment in which the Medical Management Modeler ("M3") tool is implemented and the results from which may be generated, displayed, stored and/or output. It will be understood by a person of skill in the art, however, that FIG. 1 is merely exemplary of a computer network environment in which multiple computers interconnect to an insurance system 100. Accordingly, the illustration of FIG. 1 is not meant to limit the number and types of connections to the insurance system 100.

In a manner described below, the data processing aspects of the present invention may be implemented, in part, by programs that are executed by a computer. The term "computer" as used herein includes any device that electronically executes one or more programs, such as personal computers (PCs), hand-held devices, multi-processor systems, microprocessor-based programmable consumer electronics, network PCs, minicomputers, mainframe computers, routers, gateways, hubs and the like. The term "program" as used herein includes applications, routines, objects, components, data structures and the like that perform particular tasks or implement particular abstract data types. The term "program" as used herein further may connote a single program application or module or multiple applications or program modules acting in concert. The data processing aspects of the invention also may be employed in distributed computing environments, where tasks are performed by remote processing devices that are linked through a communications network. In a distributed computing environment, programs may be located in both local and remote memory storage devices.

Insurance system 100 processes and stores information relating to health insurance plans in a manner known in the art. Such a system includes, for example, data relating to the health care history and claim history of plan participants. The system 100 also processes and stores information that permits proper payment of claims made on behalf of plan participants. As illustrated in the exemplary environment of FIG. 1, insurance system 100 may include multiple interconnected computers 102-106 and databases 108-112. The number and type of computers 102-106 and databases 108-112 are selected to meet the needs of the insurance company that administers insurance plans. Large insurance databases may include many terabytes of data and several data processing computers.

Among other things, the insurance system 100 typically stores information for each plan participant or member. Member data includes, for example, name, member identification number, address, telephone number, age, date of birth, gender, geographic region, member's medical claims, member's pharmacy claims, primary care physician (if appropriate), a last discharge from case management date, a health profile (including diseases or conditions for which the member received treatment and associated dates), and information relating to specialists (including the specialty and date last seen). Preferably, member data also comprises clinical data, which includes health related diagnosis and pharmacy data contained in a member's medical and pharmacy claims. In embodiments, member data further includes event data, such as inpatient and outpatient procedures and admissions, as well as financial data, including monetary value associated with each instance of utilization of health benefits by the member. The insurance system also maintains and stores information relating to each plan.

Data residing within insurance system 100 may be accessed, and additional data may be input, by directly connected computers, such as computer 114, or by other computers connected via a network, as is schematically illustrated by computers 116, 118 and network 120. Although the exemplary environment of FIG. 1 illustrates only a single computer directly connected to the insurance system and only two computers connected via a network, it will be understood by a person of skill in the art that a large number of computers, whether networked or directly connected to one or more computers within the insurance system 1, will be used to access data within the system or to input new data. The data of insurance system 100 also may be accessed and input via remotely located computers, such as computers 124, 126 and the Internet 122. The illustration of representative computers in FIG. 1 is not intended as a limitation on the number or types of communication with insurance system 100.

Insurance system 100 accepts, stores and acts upon data that is input by administrators and other authorized personnel. For example, information relating to insurance plans offered by the insurance organization and information relating to the individual plan participants must be input to the system. Claims by medical providers and pharmacies also must be input to the system. Likewise, claims by individuals, such as disability claims, are input to the system. The programs and applications running on insurance system 100 use the input data to reconcile premiums, benefits and claims on behalf of plan participants and medical service providers, including behavioral health service providers.

The data processing aspects of the present invention further include an information system 128, which includes a database 130 and computer 132. It will be understood by a person of skill in the art that system 128 may be implemented either as a physically separate structure or as a logically separate structure. In a manner described in more detail below, information system 128 extracts data from the insurance system 100. Computer 132 and the programs running thereon include an Internet server application and an information server that is capable of accessing information on database 130. In a highly preferred embodiment, the database engine supplier is SAS Institute Inc. ("SAS").

Additional aspects of the M3 invention, as implemented on the previously described systems, is described below by reference to the (1) underlying architecture; (2) data to information; (3) profile-matching; (4) information to prediction; (5) post prediction; (6) driver table; (7) input validation; (8) driver data purpose; (9) estimating member counts; (10) estimating prevalence rates; (11) estimating program participation; (12) estimating program fees; (13) indirect savings; (14) return on investment; and (15) the confidence limits on the return on investment.

Underlying Architecture

The invention informatics utilize SAS statistical analysis tools, which provide a foundation to a complete, comprehensive and integrated platform for:
data extraction,
interrogation,
manipulation,
pre-statistical model staging,
statistical modeling,
model training and validation,
propagation of the tool driver-tables, and,
the SAS-Internet M3 tool architecture itself.

The M3 tool SAS web-based interface allows for analytics previously available to technical users to be placed in the hands of decision makers to drive accurate and timely decisions from empirically-grounded results without assistance from modelers and statisticians. The M3 tool further provides a mechanism to model business processes (e.g. disease management) and provides powerful mechanisms for "what-if" simulation analyses. Complex processes can be simulated and a variety of scenarios tested, providing a safe means for evaluating and refining proposed policies before implementation. The M3 tool further allows for the leveraging of past trends to forecast future results. Various screen shots of the web-based graphical user interface are set forth in FIGS. 2-6 and 10.

Figure 2:
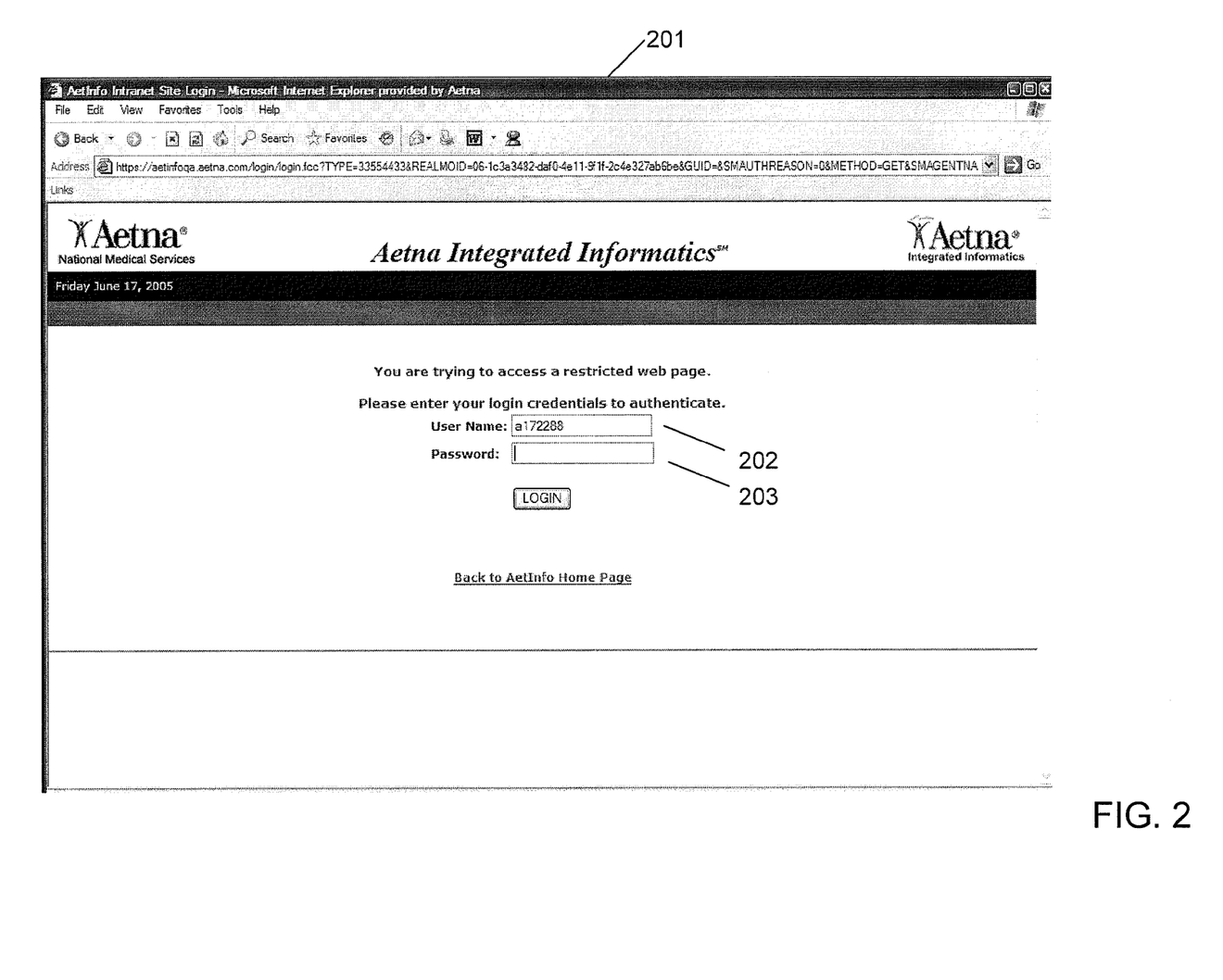
FIG. 2 illustrates an exemplary user interface displayed by a system according to an aspect of the invention that challenges a user to input credentials.
Figure 3:
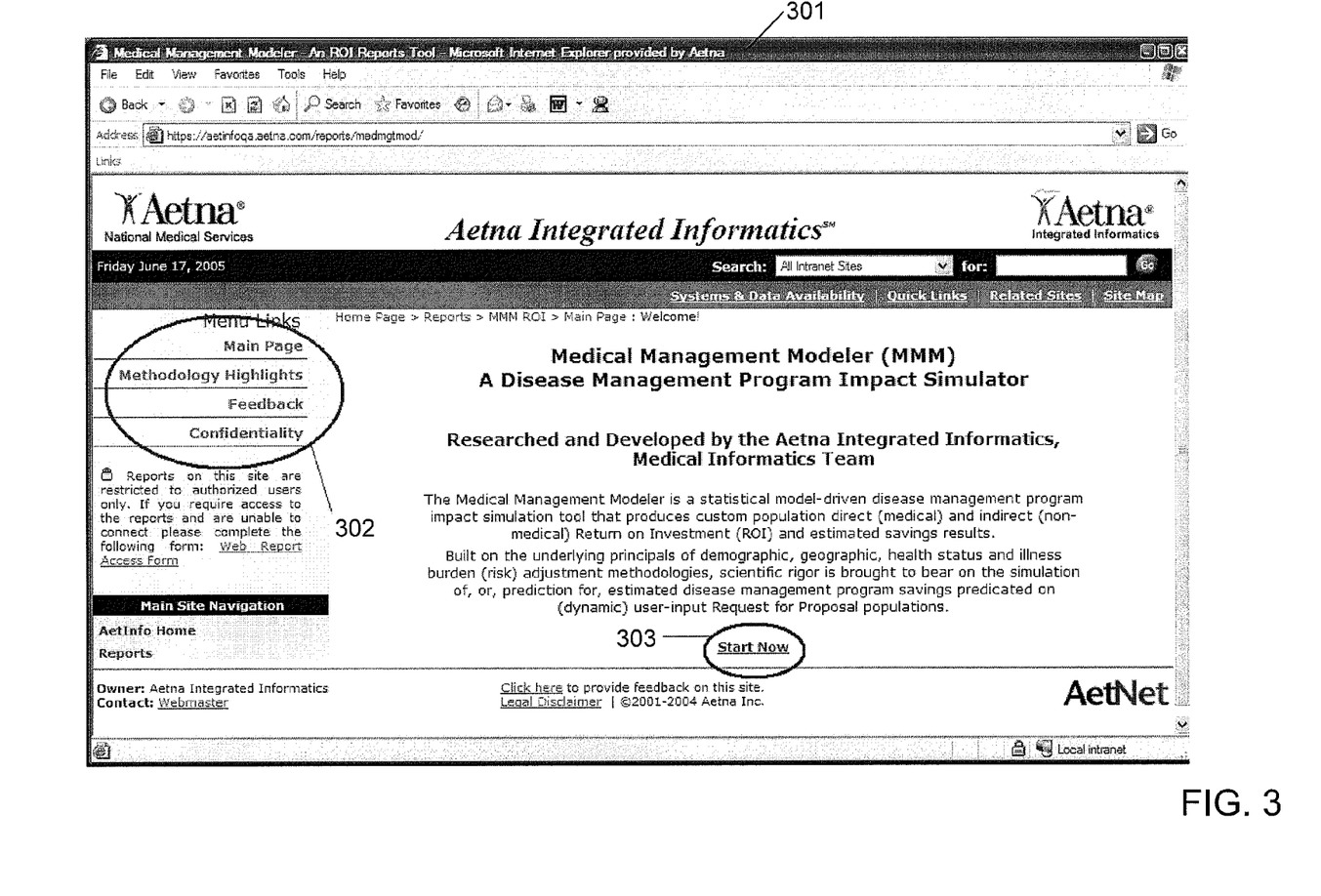
FIG. 3 illustrates an exemplary user interface displayed by a system according to an aspect of the invention that allows a user to select a further interface.

FIG. 2 illustrates a security log-in screen 201 displayed by information system 128. Due to the nature of the stored information, which is accessible through the M3 tool, any user of the system must first enter appropriate credentials, such as user name and password, as illustrated in fields 202 and 203 respectively. Upon authorizing access, information system 128 then presents a user with an integrated page 301, as illustrated in FIG. 3, that includes links to further HTML pages 302 or a link to access data within the SAS system, illustrated by link 303.

Figure 4:
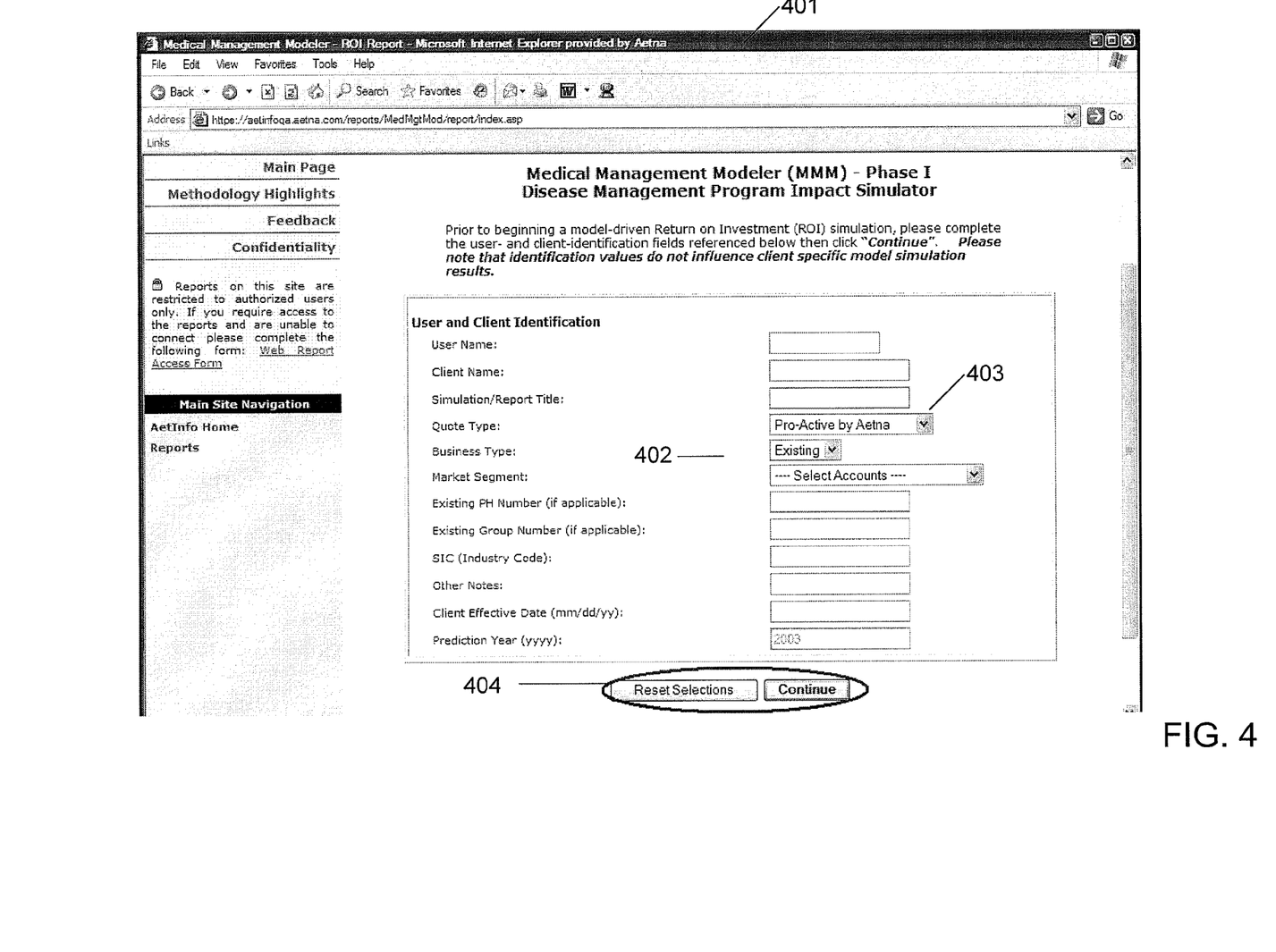
FIG. 4 illustrates an exemplary user interface displayed by a system according to an aspect of the invention that prompts a user to input the fields associated with a disease management program simulator.

Upon selecting link 303, an authorized user is thereafter presented with a further interface screen, such as that illustrated in at reference numeral 401 in FIG. 4. At this stage, the system 128 prompts the user to input the fields associated with a Phase I Disease Management Program Impact Simulator, which fields are generally indicated by reference numeral 402 and include: user name, client name, simulation/report title, quote type, business type, market segment, existing PH number and group number (if either is applicable), SIC (Industry Code), any notes that the user may seek to input, the effective date associated with the client and a prediction year for the simulation. Certain of the fields, such as the "Quote Type" field 403, may be pre-populated with information that is accessible through a drop-down menu. After the user has completed the information, the user selects the "Reset Selections" or "Continue" button, which in the exemplary embodiment have been coded with HTML and accessed through an Internet server, which then allows the user to access the next interface.

Figure 5:
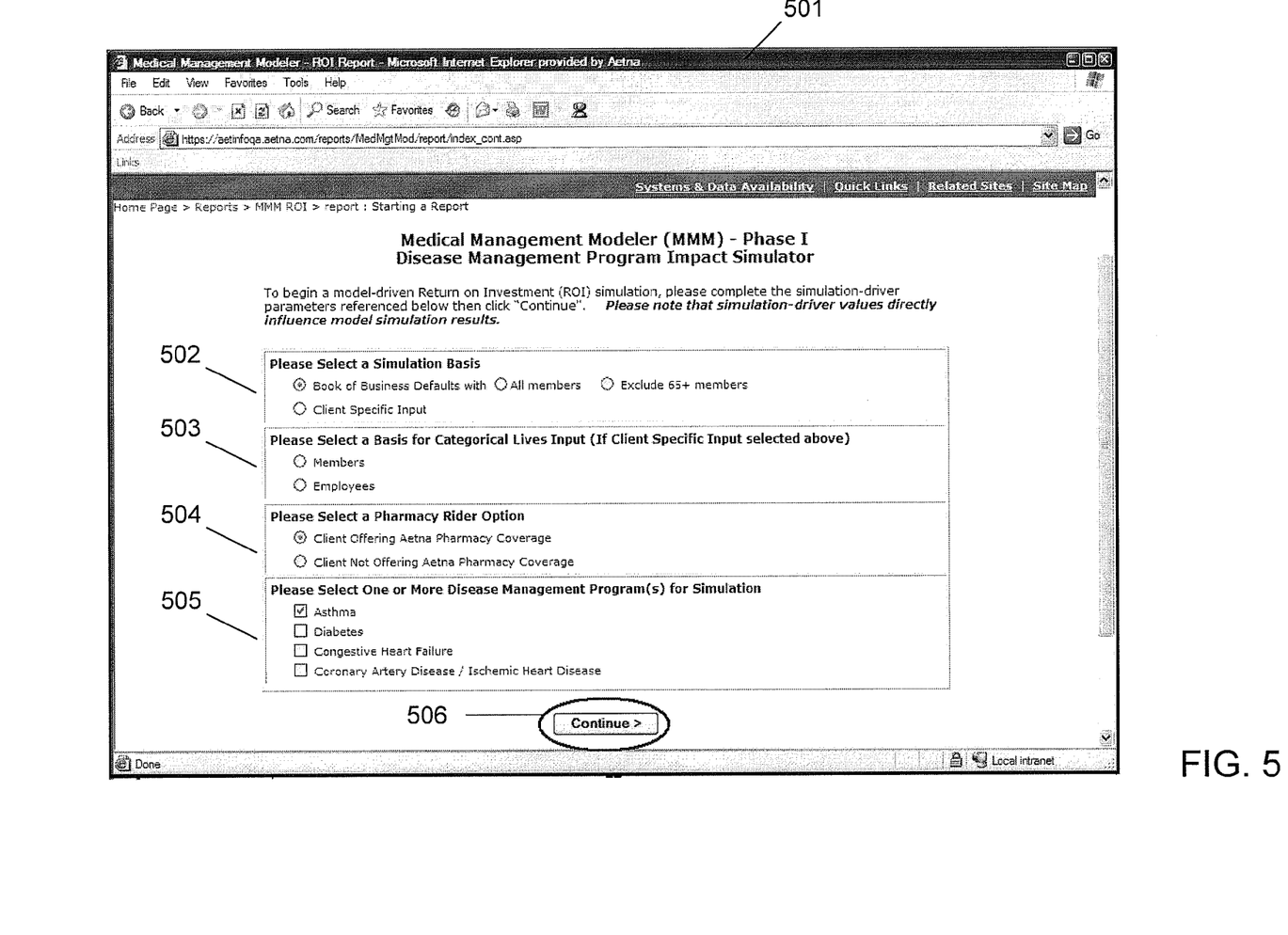
FIG. 5 illustrates an exemplary user interface displayed by a system according to an aspect of the invention that prompts a user to selects a simulation basis.

FIG. 5 illustrates an exemplary web page 501 that acts as the final gateway to the SAS web-based interface. In this interface, a user selects a simulation basis from either Book of Business Defaults or Client Specific Input, as indicated by the radio buttons in box 502. In addition, a user should further select "All Members" or "Exclude 65+ Members" if the user selects Book of Business Defaults. This setting allows the M3 tool to use all member data or exclude data from those members older than 65 years. In "Client Specific Input" has been selected in box 502, the user must then select an appropriate basis for the categorical lives input. In the example of FIG. 5, the user must select "Members" or "Employees" through this box. Next, as illustrated in box 504, the user selects whether the client is offering pharmacy coverage. In the example of FIG. 5, the interface is customized to Aetna, the assignee of the present application, due to the availability within the M3 tool of Aetna pharmacy data. Finally, in box 505, the user selects one or more disease management programs for simulation, such as Asthma, diabetes, congestive heart failure or coronary artery disease. Thereafter, the user launches the system into the SAS portion of the system by selecting the "Continue" button 506.

Figure 6:
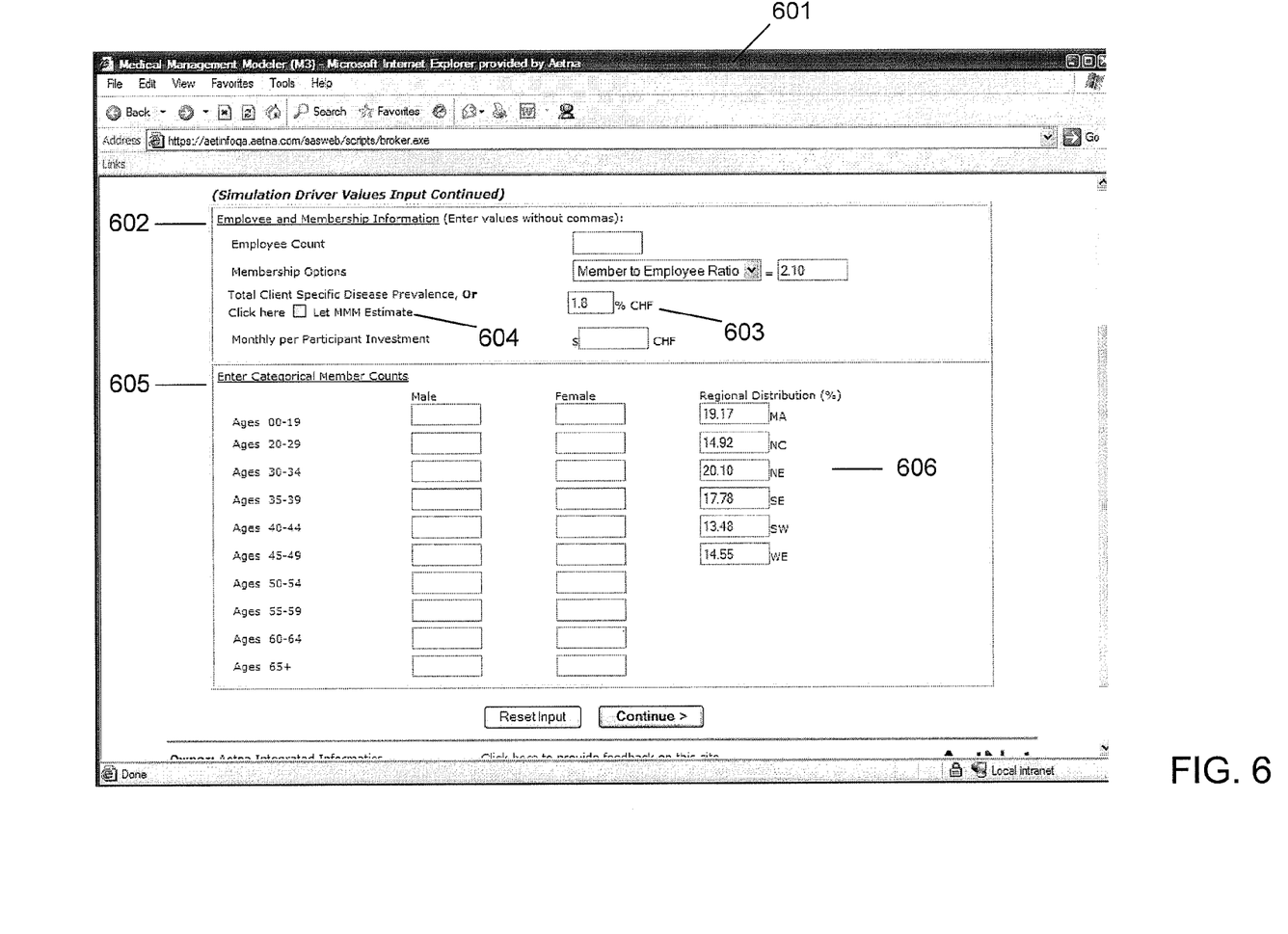
FIGS. 6-8 illustrate exemplary user interfaces displayed by a system according to an aspect of the invention that allow a user to input information relating to a client specific disease prevalence for a specific condition.
Figure 7:
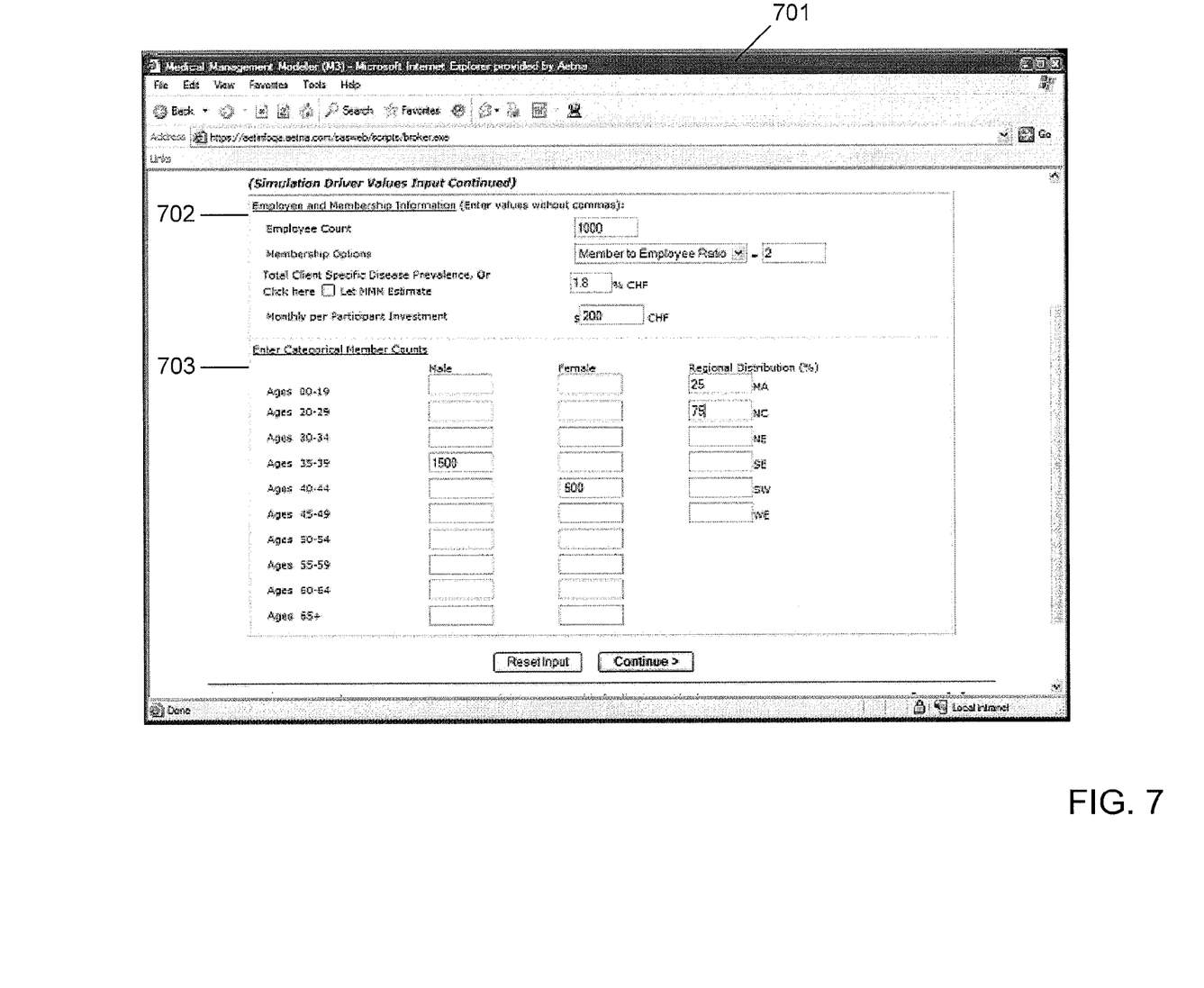

FIG. 6 illustrates a first page 601 presented by the SAS web-based interface of a preferred embodiment. Through such an interface, a user inputs simulation driver values that the M3 tool will use to determine ROI. In the exemplary embodiment of FIG. 6, which is an interface seeking input relating to a client specific disease prevalence for congestive heart failure, a user inputs data at box 602 corresponding to employee and membership information, such as employee count, membership options, disease prevalence, and monthly per participant investment amount. A user may input the "Client Specific Disease Prevalence" in input box 603 or may check input box 604 to allow the M3 tool to estimate the prevalence based on stored data. In addition, a user inputs, at box 605, a breakdown between male and female members and the counts of each by age range. Finally, at box 606, the user inputs the distribution of data by geographical region. FIG. 7 shows a similar input with different values input by a user.

Validation of user input is a feature of the preferred embodiment. Information system 128, including through the SAS tools, analyzes information input in an interface, such as that illustrated in FIG. 6, and then provides notice of any errors. For example, as indicated by reference numeral 803 in FIG. 8, a user has input data corresponding to 1000 males in the category "Ages 20-29" and 500 males in the category "Ages 35-39" for a total of 1500 members. The user had previously entered an "Employee Count" of 2500 and an "Member to Employee Ratio" of 2.1, as indicated by reference numeral 802. These two constraints do not match, i.e., 1000+500 does not equal 2500×2.1. Therefore, information system 128 would return an invalid input message. Thus, in page 901 of FIG. 9, the system returns message 902 "Total members entered does not match Total."

Data to Information

The critical analytical path from the data warehouse, such as repositories 108-112 of FIG. 1, to residence in the M3 statistical model-driven simulation tool is multi-faceted, subtle and complex. The data warehouse source data extraction is accomplished via SAS ProcSQL for the following exemplary types of information:
Medical claims
Pharmacy claims
Health Profile Database Chronic Disease Markers
Health Profile Database Prevalence and DM Eligibility Information
Symmetry Episodic Care Temporal Retrospective Risk Markers
eTUMS disease management temporal and categorical intervention information
Member demographic, geographic and health plan enrollment information
Other supplemental information Data quality, integrity and model preparation is important for producing accurate forecasts. Data collected in a transactional format (e.g. claim payment systems) is typically not structured for forecasting because, typically, it is not recorded at or for specific time intervals.

An aspect of a preferred embodiment of the invention is the conversion of transactional data by accumulating the data into the time intervals required. This is important within the framework of the M3-driver forecasting algorithms, which may use a temporally aligned "floating" intervention date for center alignment of pre v. post periods among cohort populations.

The data also may be aggregated by member with a series of continuous (e.g. age), categorical (e.g. risk) and dichotomous (e.g. presence/absence of a cardiac cluster) explanatory variables to serve as components of profile-matching as well as model covariates (i.e. characteristics that potentially explain variance in costs and utilization). Further, views of the degree of normality regarding the data distribution facilitates an efficient isolation and quantification of the outlier membership, which can confound precise forecasting estimates.

Figure 10:
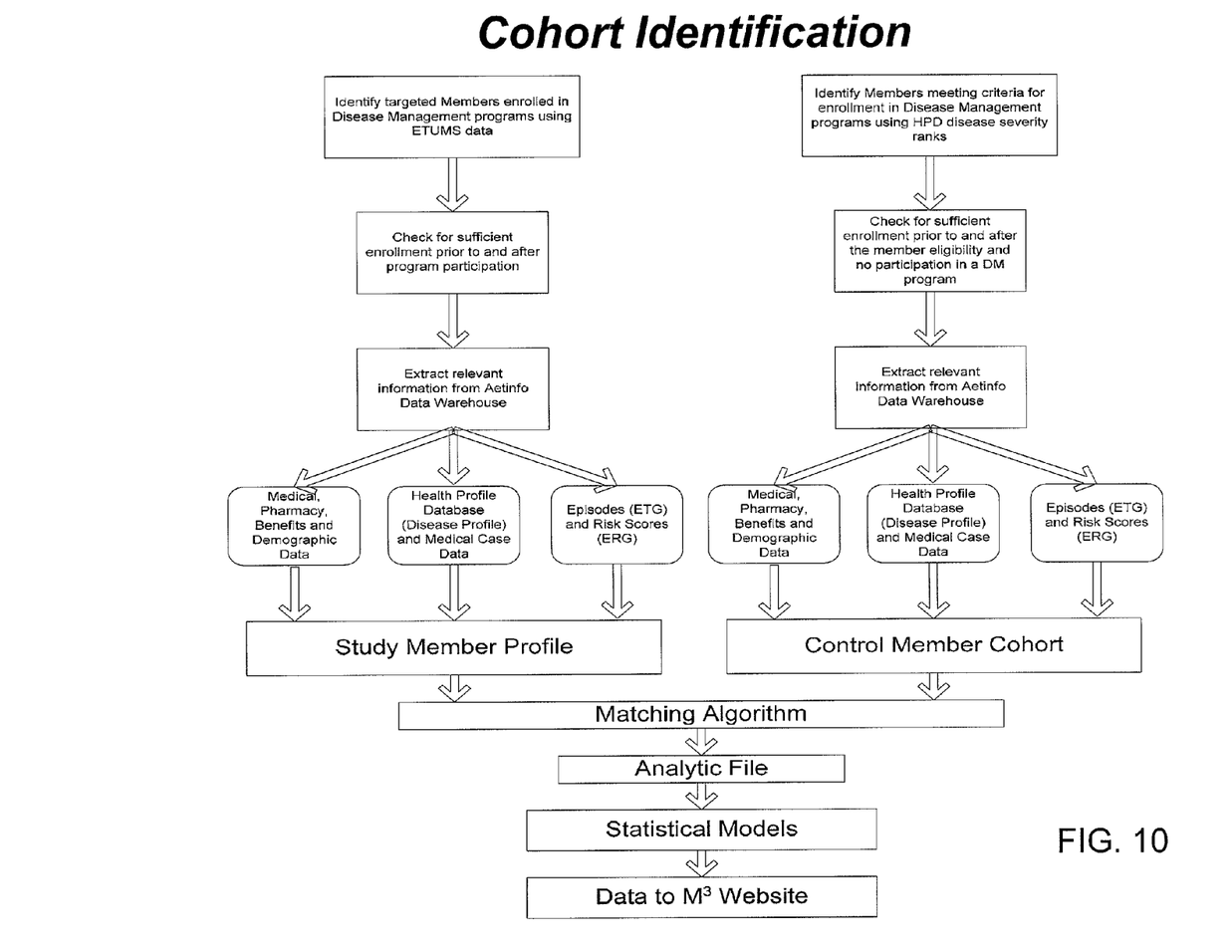
FIG. 10 illustrates a flow diagram associated with an exemplary method for obtaining, accumulating, generating and aggregating data and otherwise preparing a study member profile and a suitable control member cohort.

The steps of obtaining, accumulating, generating and aggregating data and otherwise preparing a study member profile and a suitable control member cohort are further described in FIG. 10.

Profile-Matching

Given the criticality of constructing appropriate comparator cohorts, the invention includes a refined "Risk-Sensitive Profile-Matching" algorithm. The algorithm first categorizes each of the identified fund study cohort members into one of, potentially, thousands of unique clinical/risk/demographic/geographic "keys". Each key is comprised of a unique combination of the following member "characteristics":
Age category with Gender
Region
Product (HMO v. non-HMO)
Asthma (presence or absence of)
Cardiology cluster (presence or absence of)
Hypertension (presence or absence of)
Oncology cluster (presence or absence of)
Remaining acute condition cluster (presence or absence of)
Remaining chronic condition cluster (presence or absence of)
Other conditions (presence or absence of)
Symmetry episodic care categorical retrospective risk score (1-5)

Once established, the unique study cohort keys are constructed and then applied to a randomly-derived Book of Business ("BOB") sample. Clinical, risk, demographic and geographic profile-matched control members are found for each of the study members.

Those study members who could not be matched using the most rigorous criteria are matched in a stepwise fashion using successively less robust matching criteria. The sample, once profile-matched to the study cohort, becomes a "Control"

population, realizing an approximate 2:1 control to study cohort member ratio. Once the "full" key matching potentials have been exhausted, a highly iterative process of matching on "full-key subsets," winnowed predicated on clinical importance, follows.

Information to Prediction

A preferred embodiment of the invention includes predictive statistical modeling via, the SAS Stat tool. This tool includes the detection and adjustment of "outlier" data.

More specifically, the history of each item being forecast is examined, and outliers and shifts in data can be automatically identified. Subsequent forecasts can be adjusted accordingly for the outliers and shifts, preventing spurious results due to abnormalities in the data. Once the data have been appropriately structured, the staged, temporally aligned information is run through a series of custom predictive models.

A predictive model is thereafter defined by the utilization of a characteristically profile-matched control population to derive a forecast equation. This equation includes "pre-period characteristics" and "post period dollars." Post profile-matching, the difference between the control and study populations is the presence of a disease management intervention.

The application of the profile-matched control population derived equation to the study (i.e. intervention) population yields an expectation of what the study cohort should have cost, by member, in the absence of the intervention. The difference between the study actual and the predictive modeled expectation is the savings or loss for a given member or aggregate population.

Post Prediction

The invention includes a tools for post-prediction data aggregation (i.e. Driver-Table) and tool propagation processes. Application of the statistical model equations predict a post intervention period cost for each member individually.

Once determined, each member is categorized into one of a series of "dimension clusters" that are predicated on every possible permutation of the dynamic user input:
  Chronic disease (i.e. Diabetes, CHF, Asthma, CAD),
  Categorical age,
  Gender,
  Presence or Absence of Drug Rider, and,
  Region Once the applicable dimension clusters are populated, a statistically derived minimum threshold is calculated. The threshold represents the minimum number of members slotted into a given dimension cluster that warrants statistical confidence in the predicted value for members in that cluster in the aggregate.

Once determined, dimension clusters not rising to the minimum threshold are coupled with adjacent clusters to achieve or surpass the minimum threshold, thereby allowing for confidence in the "blended" dimension cluster result.

Driver-Table

Once the M3 Driver-Table has been statistically tested, the dimension cluster aggregate predictions are ported into a Internet architecture for efficient querying and simulation of savings predictions and Return on Investment (ROI) values. This is illustrated, for example, in FIGS. 2-7.

Given the imprecise nature of cost prediction, the invention calculates upper and lower bound 95% confidence intervals for each disease specific savings and ROI value. The 95% upper and lower bound confidence intervals are interpreted as follows; there is a 95% certainty that the realized savings/ROI will fall within the prescribed range of values. If the upper and lower bound confidence intervals cross the value of zero, the result is not statistically significant.

Input Validation

Figure 8:
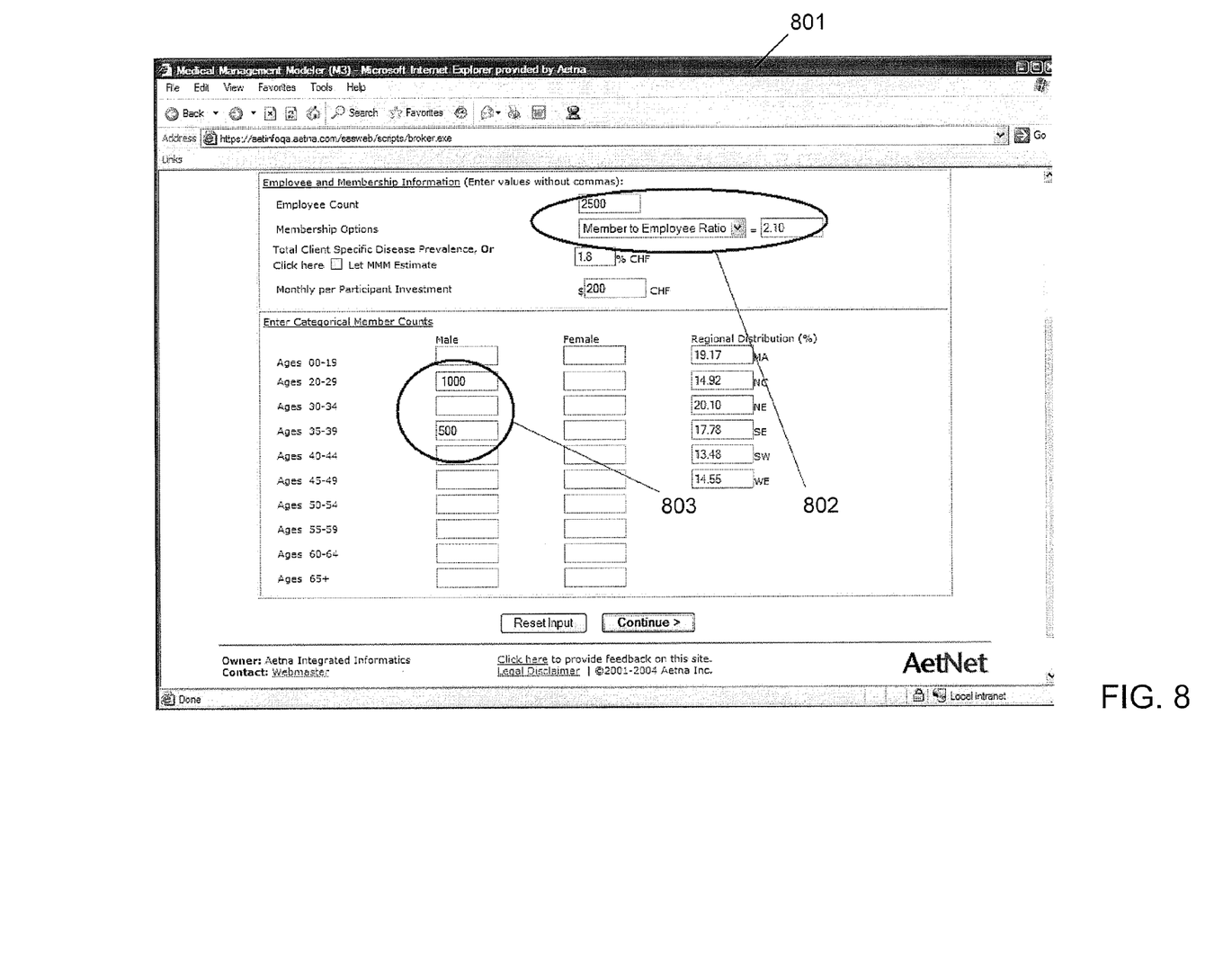
Figure 9:
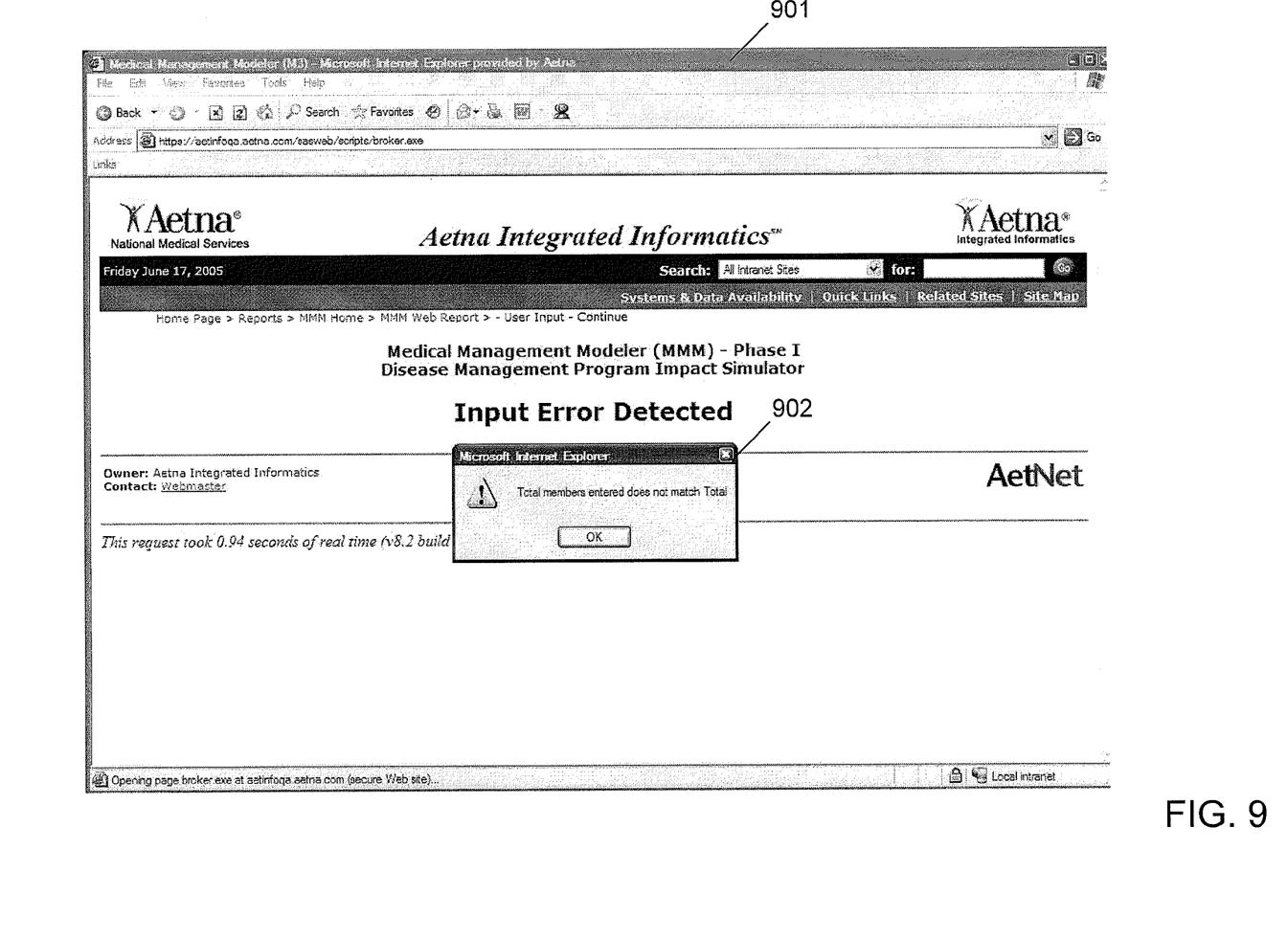
FIG. 9 illustrates an exemplary error message displayed in response to user information.

FIGS. 7 and 8, as noted above, illustrate a GUI of an exemplary embodiment of the invention for the purpose of input validation. If the check box "BoB defaults" is selected, then either 'All Members' or 'Exclude 65+ Members' is selected. If "Client Specific Input" is selected, then either an input basis of 'Members' or 'Employees' is selected. At least one disease management program is selected for simulation. The following tests against user input may be conducted, among others:
  Employee Count is Positive
  'Monthly Per Participant Investment' is positive.
  Either a positive disease prevalence is entered, or the 'Let MMM Estimate' checkbox is entered.
  Distribution by region sums to 100%
  For all four input methods, an empty age/gender bucket will default to 0 (count or percent). It is not required to populate all buckets, only to ensure that all populated buckets sum as described below:
  Note that there are two 'Membership Options'. 1) Member Count; 2) Member to Employee Ratio
  Total Member Count entered in the age/gender buckets sums to the Member Count entered. Member Count and all age buckets must contain positive numbers; or . . . .
  The product of the employee Count and the Member to Employee Ratio sums to the Total Member Count entered in the age/gender buckets. Member to Employee ratio must be greater than 1.00.

Similar validation exists for other demographic input methods (Member Percent, Employee Count, Employee Percent). A difference between the validations, however, is what the numbers input in the age/gender buckets must add to. For the Member Percent and Employee Percent, age/gender buckets with data must be positive and add to 100 percent. For the Employee Count input screen, age/gender buckets with data must be positive and add to the Employee Count in the first field.

Driver Data Purpose

This aspect of the invention includes the step of estimating the number of members in each of 240 different strata with the given Gender, Age Category, Region, and a Drug Rider. For example, estimate the number of Males Age 30-34 in Mid-Atlantic, the number of Females Age 30-34 in Mid-Atlantic, etc.

The output prevalence rates, eligibility rates, active participation rates, and program savings are the weighted averages of the corresponding field for each row in the table. The pooled standard deviation of the program savings is also calculated. A simplified example may include 200 Males aged 30-39 in West Region, 100 Females age 20-24 in North Central Region. Assume on the DRIVERDATA, the "asthma program" savings are $50 and $30 for these strata respectively. The reported savings for such an example would be given by the following expression: [200($50)+100($30)]/(200+100)=$43.33

Sample driver data tables for both Primary Key (Table 1) and Other Fields (Table 2) are reproduced below:

TABLE 1

PRIMARY KEY

| Column | Data type | Valid Values | Description |
|---|---|---|---|
| gender | Char(3) | F, F/M, M | Gender |
| region | Char(11) | All Regions, MA, NC, NE, SE, SW, WE | Region |
| age cat | Char(8) | 00-19, 20-29, 30-34, 35-39, 40-44, 45-49 50-54, 55-59, 60-64, 64+, All Ages | Age Category |
| drug rider | Char(3) | N, Y | Drug Rider |

TABLE 2

OTHER FIELDS

| Column | Data type | Description |
|---|---|---|
| XXX__prevalance | | Disease Prevalence Rate for the given stratum for disease XXX |
| XXX__eligible | Num(8) | Proportion of Prevalent Members Eligible for DM Program for disease XXX (eliminates false positives using HPD flag) |
| XXX__par__rate | Num(8) | Proportion of Eligible Members Participating in DM Program for disease XXX |
| XXX___pgm__svgs | Num(8) | Estimated Mean Program Savings for DM Program for disease XXX. |
| XXX__std | Num(8) | Estimated Standard Deviation of Mean Program Savings for DM Program for disease XXX |
| Tot__Members | Num(8) | Count of Members in this Stratum in the BoB |
| Dia__CHF__Com | Num(8) | Percentage Overlap among Diabetes and CHF Members in this Stratum |

The following additional fields are either deprecated or used for QA: Avg_Dem_Risk, Avg_Ret_Risk, Avg_Pro_Risk, XXX_invest_pmpm Driver Data Estimating Member Counts The invention calculates $n_{ijkR}$ which corresponds to the estimated membership for the given plan sponsor in Age Group i, Gender j, Region k and Rider R. Four input screens leads to four ways to calculate $n_{ijkR}$:

1. Input Member Counts

Let $ageGdrCnt_{ij}$ denote the number of members input in the bucket for Age Group i and Gender j and let $rgnPct_k$ denote the percentage of members in Region k. Then $n_{ijkR} = ageGdrCnt_{ij} \times rgnPct_k$ 2. Input Member Percentages Let $ageGdrPct_{ij}$ denote the percentage of members input in the bucket for Age Group i and Gender j and let $rgnPct_k$ denote the percentage of members in Region k. Let CSMbrs equal the number of members input for the given client. Then $n_{ijkR} = ageGdrPct_{ij} \times rgnPct_k \times CSMbrs$ If inputting Employee counts or percentages, it may be necessary to estimate member counts. Typically, it is not preferred to assume that age-gender distribution of dependents is the same as employees (dependents will be younger).

In addition, the $BOBdepRate_{ij}$ is the expected percentage of dependents with Age Group i and Gender j for an employee in the BOB. These values are stored in a table called AGE_CAT_ONLY with three fields: age_cat, gender, and rate ($BOBdepRate_{ij}$): $BOBdepRate_{ij}$ has the following properties: $BOBdepRate_{iM} = BOBdepRate_{iF}$. This assumes that the distribution is the same for male and female dependents.

$$\sum_{ij} BOBdepRate_{ij} = 2$$

$$\sum_{i} BOBdepRate_{iG} = 1$$

The book of business dependency rates are further set forth in Table 3 below:

TABLE 3

BOBdepRate$_i$.

| i | BOBdepRatei. | I | BOBdepRatei. |
|---|---|---|---|
| 00-19 | 0.5344 | 45-49 | 0.0610 |
| 20-29 | 0.0919 | 50-54 | 0.0527 |
| 30-34 | 0.0455 | 55-59 | 0.0446 |
| 35-39 | 0.0569 | 60-64 | 0.0283 |
| 40-44 | 0.0642 | 64+ | 0.0204 |

3. Input Employee Counts

Let $empAgeCnt_{ij}$ denote the number of employees with Age Group i and Gender j as input in the age-gender buckets. Based on the input employee demographic data the number of members in each stratum may be estimated by a several step process. First, the number of dependents in each stratum is estimated, and this is added to the number of employees in each stratum. Denote the number of dependents in stratum with Age Group i, Gender j, and Region k as $dep_{ijk}$.

$$dep_{ijk} = \frac{BOBdepRate_{ij} \times rgnPct_k \times CSEmployees \times (CSmbrEmpRatio - 1)}{200}$$

$$n_{ijk} = \frac{empAgeGdrCnt_{ij} \times rgnPct_k}{100} + dep_{ijk}$$

4. Input Employee Percentages

The fourth input differs from the preceding inasmuch as instead of empAgeGdrCntij being input, it must be calculated from the percent of employees in each age bucket. So in the equation for $n_{ijk}$ above, replace $empAgeGdrCnt_{ij}$ with the following expression:

$$empAgeGdrCnt_{ij} = \frac{CSEmployees \times empAgeGdrPct_{ij}}{100}$$

Estimating Prevalence Rates

The invention further provides for estimating prevalence rates according to the following protocol:

Denote the Client-Specific prevalence rate (for Age Group i, Gender j, Region k, and Drug Rider R) as $CSprev_{ijkR}$, and denote the BoB prevalence rates (the rates stored in the DRIVERDATA table as BOBprev$_{ijkR}$. In addition, the following two numbers must be determined: CSprev (the overall Client-Specific prevalence rate) and CSprev$_{ijkR}$ (the Client-Specific prevalence rate for each row).

If the M3 tool defaults are selected, e.g., the "Let M3 Estimate" checkbox is checked, CSprev is unknown and CSprev$_{ijkR}$ is equal to BOBprev$_{ijkR}$. In such circumstances, the BOB overall prevalence rate will be calculated BOBprev as:

$$BOBprev = \frac{\sum_{ijk}(n_{ijkR}BOBprev_{ijkR})}{\sum_{ijk}(n_{ijkR})}$$

and CSprev is set equal to BOBprev.

If the 'Let M3 Estimate' checkbox is not checked, the user is inputting CSprev, and it is the CSprev$_{ijkR}$ that are unknown. In this event, all stratum-specific prevalence rates for the client are proportional to the BOB prevalence rates by the same factor at, i.e. CSprev$_{ijkR}=\alpha$(BOBprev$_{ijkR}$):

$$CSprev = \frac{\sum_{ijk}(n_{ijkR}CSprev_{ijkR})}{\sum_{ijk}(n_{ijkR})}$$

$$CSprev = \frac{\sum_{ijkR}(n_{ijkR}\alpha(BOBprev_{ijkR}))}{\sum_{ijkR}(n_{ijkR})} = \alpha(BOBprev)$$

$$\alpha = \frac{CSprev}{BOBprev}$$

$$CSprev_{ijkR} = \frac{CSprev}{BOBprev}BOBprev_{ijkR}$$

CSprev$_{ijkR}$ is thereby determined in terms of known quantities.

The Prevalence Rates within age groups are the last charts produced, which charts may be rendered in HTML and PDF output and/or a table in Excel form. CSprev$_i$, the client-specific prevalence rate for Age Group i, will typically be of most significance. This value may be calculated by determining the weighted sum of the stratum-specific prevalence rate within each Age Group i for all the values of Gender j and Region k.

$$CSprev_i = \frac{\sum_{jk}((n_{ijkR})(CSprev_{ijkR}))}{\sum_{jk}(n_{ijkR})}$$

Estimating Program Participation

Let BOBelg$_{ijkR}$ be the BOB percentage of members for a given stratum with the disease who are eligible for the Disease Management program. (These are the members with the multiple indications of the disease that are helpful to eliminate false positives.)

Let BOBpar$_{ijkR}$ be the BOB percentage of eligible members (as defined above) who participate in the Disease Management program.

Let BOBpgmSvg$_{ijkR}$ be the BOB program savings of participating Members in the given stratum.

For disease XXX, these values are is stored in the XXX_eligible, XXX_par_rate, and XXX_pgm_svgs fields of the DRIVERDATA table. The values CSelgMbr, CSparMbr, and CSpgmSvgs, i.e. the estimated number of eligible members, participating members, and program savings for the given plan sponsor, may be calculated as follows:

$$CSelgMbr = \sum_{ijk}((n_{ijkR})(BOBelg_{ijkR})(CSprev_{ijkR}))$$

$$CSparMbr = \sum_{ijk}((n_{ijkR})(CSprev_{ijkR})(BOBelg_{ijkR})(BOBpar_{ijkR}))$$

$$CSpgmSvgsPerMonth = \left(\sum_{ijk}\binom{(n_{ijkR})(CSprev_{ijkR})(BOBelg_{ijkR})}{(BOBpar_{ijkR})(BOBpgmSvg_{ijkR})}\right)$$

$$CSpgmSvgs = 12 CSpgmSvgsPerMonth$$

Estimating Program Fees

The 'Program Investment' column is calculated using the previous calculation for CSparMbr.

$$CSparMbr = \sum_{ijk}((n_{ijkR})(CSprev_{ijkR})(BOBelg_{ijkR})(BOBpar_{ijkR}))$$

CSFeesPerParMbrPerMonth is input by the user. To calculate the total fees, multiply the number of participating members by the fees per participating member per month (user input) by 12 months.

CSpgmFees=CSparMbr×CSFeesPerParMbrPerMonth×12

Indirect Savings

Indirect Savings, such as that based on lack of absenteeism and increased productivity, may be generally calculated according to known methodologies, such as that described by Goetzel R G et al (2003), The Health and Productivity Cost Burden of the "Top 10" Physical and Mental Health Conditions Affecting Six Large U.S. Employers in 1999, JOEM. 45(1):5-14, which is hereby incorporated by reference in its entirety. In addition, it is possible to apportion total health care costs into direct and indirect costs for a given disease D. Note that IndTotalRatio$_D$ is a percentage (i.e., is between 0 and 100). By definition:

$$\frac{IndTotalRatio_D}{100} = \frac{indirectCostsPEPM_D}{directCostsPEPM_D + indirectCostsPEPM_D}$$

Solving for indirectCostsPEPM$_D$ gives $$indirectCostsPEPM_D = \frac{(IndTotalRatio_D)(directCostsPEPM_D)}{100 - IndTotalRatio_D}$$

These values may further be calculated from Goetzel or actual claims data:

From Goetzel et al (Table 3) From actual claims data
indirectCostsPEPMAST=46 directCostsPEPMAST=511
indirectCostsPEPMCHF=13 directCostsPEPMCHF=1211
indirectCostsPEPMDIA=28 directCostsPEPMDIA=863.10
indirectCostsPEPMCAD=13 directCostsPEPMCAD=1199

Goetzel's coefficients are determined per participating employee. The calculation of these coefficients differs slightly depending on whether member or employee counts input. For member input, it is possible to denote $emp_{ijkR}$ as the number of employees with Age Group i, Gender j, Region k, and Drug Rider R. In the SAS dataset EMP_AGE_RATE is stored the default Age Gender distribution of employees. This table has keys age_cat and gender and also has the field rate, $BOBempAgeGd_{rij}$, which stores the percentage of employees:

$$\sum_{ij} BOBempAgeGdr_{ij} = 1$$

The number of employees participating in the program may be estimated by multiplying the stratum-specific prevalence, eligibility, and participation rate by the estimated number of employees in each stratum.

$$CSparEmp = \sum_{ij} \text{round}\left[\frac{(CSEmployees)(BOBempAgeGdr_{ij})}{(BOBprev_{ijAllRegionR})(BOBelg_{ijAllRegionR})(BOBpar_{ijAllRegionR})}\right]$$

If the user is inputting employee counts or percentages, then it is straightforward to calculate the number of employees in each stratum, and these actual numbers are multiplied by the stratum-specific prevalence, eligibility, and participation rate to get CSparEmp.

ROI

Once the foregoing calculations have been made, the Return on Investment calculation may be performed according to the following formula:

$$CSdirectROI = \frac{CSpgmSvgs}{CSpgmFees}$$

The indirect savings can be added to the direct program savings to give:

CSTotalPgmSvgs=CSpgmSvgs+indirectCostsTotal and

CSTotalPgmSvgs=CSpgmSvgs+indirectCostsTotal

ROI (Confidence Limits)

The confidence intervals for the direct ROI are calculated as follows, which includes the step of denoting the number of participating members in each stratum as:

$parMbr_{ijkR}=((n_{ijkR})(CSprev_{ijkR})(BOBelg_{ijkR})(BOBpar_{ijkR}))$

First, the Sum of Squares for the individual strata are reconstructed.

$PgmSVgSS_{ijkR}=(pgmSvgStd_{ijkR})^2 \text{round}(parMbr_{ijkR}) \text{round}(parMbr_{ijkR}-1)$ Next, a pooled Standard Error is calculated from the individual Sums of Squares. In the equation below, grpDf represents the number of strata with non-zero members.

$$CSSvgStdErr^* = \sqrt{\frac{\sum_{ijk} pgmSvgSS_{ijkR}}{(CSparMbr - grpDf)(CSparMbr - 1)}}$$

Calculate this term so all costs are per participating member per month:

$$CSPgmSvgsPerParMbrPerMonth = \frac{CSPgmSvgsPerMonth}{CSparMbr}$$

$$CSSvgConfidenceLimits = \frac{CSPgmSvgsPerParMbrPerMonth \pm 1.96(CSSvgStdErr)}{CSFeesPerParMbrPerMonth}$$

Accordingly, a method and system for determining custom population Return on Investment (ROI) forecasted savings estimates for use in evaluating the desirability of active health care management programs and the depth of penetration of such programs has been disclosed. Those skilled in the art will appreciate that variations to the above invention may be employed without departing from the spirit and scope of the teachings herein. The scope of protection, therefore, should not be limited to the above currently preferred embodiments. Instead, the invention is intended to extend to the appended claimed subject matter, which is also made part of this disclosure.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method for calculating a potential return on investment associated with a disease management program comprising computer implemented steps of:
   querying, by a medical management modeling computer, a user to input data relating to a study population that is linked to a potential investment in a disease management program;
   validating, via the medical management modeling computer, data associated with the study population;
   obtaining, via the medical management modeling computer, cost and participation data associated with the disease management program;
   determining, via the medical management modeling computer, a control member cohort by:
      electronically selecting a random sample population from a medical insurance member database;
      constructing a plurality of unique cohort keys, each cohort key comprising one or more member characteristics selected from the group consisting of age category, gender, member geographic region, insurance product associated with the member, a dichotomous indicator of one or more predetermined diseases or conditions associated with the member, and a retrospective risk score associated with the member; and
      applying the cohort keys to the random sample population to identify the control member cohort;
   the medical management modeling computer further performing the following steps:
      (a) calculating expected costs for individual members of the study population through use of at least one control equation that uses the validated study population data and data associated with the control member cohort as inputs;
      (B) calculating aggregate expected savings associated with the disease management program;
      (c) calculating expected fees associated with the disease management program;
      (d) calculating the potential return on investment by dividing the expected savings by the expected fees;
      (e) calculating statistical confidence limits associated with the potential return on investment and
      (f) presenting the user with a result of the calculations.

2. The method according to claim 1, wherein the expected costs are insured medical costs that an individual in the study population would expect to incur after an intervention in one or more disease management programs.

3. The method according to claim 2 further comprising the step of estimating the insured medical costs associated with an individual in the absence of an intervening disease management program.

4. The method according to claim 1, wherein the aggregate expected savings is the aggregate difference between the expected costs for individual members of the study population and estimated medical costs associated with an individual in the absence of an intervening disease management program.

5. The method according to claim 1, wherein the disease management program is directed to a disease selected from a group of asthma, diabetes, congestive heart failure and coronary artery disease.

6. The method according to claim 1, wherein the control member cohort is profile matched to the study population.

7. The method according to claim 1 further comprising estimating the prevalence rates of disease in the study population.

8. The method according to claim 4 further comprising estimating the program participation rates for individuals in the study population.

9. The method according to claim 1, wherein querying a user includes displaying on a computer display a graphical user interface.

10. A method for calculating a potential return on investment associated with a disease management program comprising computer implemented steps of:
    determining, via a medical management modeling computer, a control member cohort by:
       electronically selecting a random sample population from a medical insurance member database;
       constructing a plurality of unique cohort keys, each cohort key comprising one or more member characteristics selected from the group consisting of age category, gender, member geographic region, insurance product associated with the member, a dichotomous indicator of one or more predetermined diseases or conditions associated with the member, and a retrospective risk score associated with the member; and
       applying the cohort keys to the random sample population to identify the control member cohort;
    the medical management modeling computer further performing the following steps:
       (a) calculating expected costs for individual members of a study population through use of at least one control equation that uses data associated with a control member cohort as an input;
       (b) calculating expected fees associated with the disease management program;
       (c) calculating aggregate expected savings associated with the disease management program;
       (d) calculating a potential return on investment by dividing the expected savings by the expected fees;
       (e) calculating the statistical confidence limits associated with the potential return on investment and
       (f) presenting a user with a result of the calculations.

11. A system for calculating a potential return on investment associated with a disease management program, the system comprising:
    means for identifying a disease management program and obtaining cost and participation data associated with the disease management program;
    means for determining a study population that is linked to a potential investment in the disease management program;
    means for validating data associated with the study population;
    means for determining a control member cohort by:
       (a) electronically selecting a random sample population from a medical insurance member database;
       (b) constructing a plurality of unique cohort keys, each cohort key comprising one or more member characteristics selected from the group consisting of age category, gender, member geographic region, insurance product associated with the member, a dichotomous indicator of one or more predetermined diseases or conditions associated with the member, and a retrospective risk score associated with the member; and (c) applying the cohort keys to the random sample population to identify the control member cohort;

means for calculating expected costs for individual members of the study population through use of at least one control equation that uses the validated study population data and data associated with the control member cohort as inputs;

means for calculating expected fees associated with the disease management program;

means for calculating aggregate expected savings associated with the disease management program;

means for calculating a potential return on investment by dividing the expected savings by the expected fees; and means for calculating the statistical confidence limits associated with the potential return on investment.

12. The system according to claim 11, wherein the expected costs are an expectation of insured medical costs that an individual in the study population would expect to incur after an intervention in one or more disease management programs.

13. The system according to claim 12 further including means for estimating the insured medical costs associated with an individual in the absence of an intervening disease management program.

14. The system according to claim 11, wherein the aggregate expected savings is the aggregate difference between the expected costs for individual members of the study population and estimated medical costs associated with an individual in the absence of an intervening disease management program.

15. The system according to claim 11, wherein the disease management program is a directed to a disease selected from a group of asthma, diabetes, congestive heart failure and coronary artery disease.

* * * * *